United States Patent [19]

Armstrong

[11] Plant 4,865

[45] Jul. 13, 1982

[54] FREESTONE PEACH

[75] Inventor: David L. Armstrong, Orange, Calif.

[73] Assignee: Armstrong Nurseries, Inc., Ontario, Calif.

[21] Appl. No.: 196,024

[22] Filed: Oct. 10, 1980

[51] Int. Cl.[3] ..... A01H 5/00

[52] U.S. Cl. ..... Plt./42

[58] Field of Search ..... Plt./42

*Primary Examiner*—James R. Feyrer

*Attorney, Agent, or Firm*—William H. Elliott, Jr.

[57] ABSTRACT

A peach tree of the freestone class, a moderately vigorous growth habit, bearing fruit which is somewhat larger than average, generally globose in form, and with creamy white flesh, maturing in mid-August in southern California, and characterized by its good eating quality, good keeping quality, and good shipping quality.

1 Drawing Figure

This invention relates to the discovery and asexual reproduction of a new variety of freestone peach. The fruit of this variety is juicy. It has a pronounced and pleasant aroma. Its creamy-white flesh is of melting texture, and a mild and sweet flavor. It ripens in mid-August, in southern California and is best harvested between the twelfth and twenty-fifth of that month.

The new variety was discovered by David L. Armstrong, in the fields of Armstrong Nurseries, and was reproduced by him in Wasco, Calif., where he asexually reproduced it by budding. The first plant was the result of a planned cross breeding of the peach Rio Oso Gem, U.S. Plant Pat. No. 84, as the seed parent with pollen of the peach Redwing, U.S. Plant Pat. No. 621.

The generic name, or "denomination" of the new variety is "Armdelawhip".

Among the ways in which the new variety differs from its seed parent, Rio Oso Gem, may be mentioned the fact that it is white-fleshed whereas the seed parent is yellow-fleshed. The fruit of the new variety ripens, usually, about one or two weeks later than that of Rio Oso Gem. The tree of the new cultivar is notably more vigorous than the tree of the seed parent, and its flowers are relatively small, of a salmon-pink color and not showy, whereas flowers of the Rio Oso Gem are larger, showy and light pink in color.

Among the ways in which the new variety is distinct from its pollen parent may be mentioned the later ripening season of the new cultivar. "Redwing", the pollen parent, usually ripens in or about the third or fourth week of June, whereas this new cultivar ripens considerably later, usually in the second or third week of August. The fruit of the new variety is generally somewhat larger than that of Redwing and bears less of a blush on its skin than does the fruit of the pollen parent.

The accompanying drawings show, in full color, a leaf cluster of the new variety, full views of the stem end and pistil point of a fruit, and opposite sides of a section through the plane of the suture, the stone being included in one view. In the description that follows, and which relates to a tree grown in the Wasco district, color designations beginning with a small letter are used when the name of that color, as used in common speech, is aptly descriptive. Color designations beginning with capital letters represent values based on the Nickerson Color Fan, put out by Munsell Color Company.

TREE

The tree is of medium size, of upright-spreading habit, and of moderately vigorous growth. Its foliage is dense, and the shape is round. Its hardiness has not yet been tested, but in the Wasco district it is very productive and bears regularly. The trunk is neither stocky nor slender, but intermediate. Its branches are of medium caliper, and are moderately smooth. They are semi-glossy, and their color varies from near Strong Yellow Green 5GY6/8 to near Moderate Brown 7.5YR4/5. The lenticels are few in number, and of medium size.

LEAVES

The leaves, which are of medium thickness, vary from 5½" to 8" in length and from about 1¼" to 2" in width. The form is lanceolate, and acutely pointed. The color is dark green. The leaf surface varies from smooth to slightly rugose, and the leaf margins are finely serrate and somewhat undulate. The petiole is of medium length and thickness. There are usually about 4 glands, alternately arranged, of medium size and mostly reniform in shape. The stipules fall off early.

BUDS AND FLOWERS

The flower buds are obtuse in shape and medium in size. Their hardiness is untested.

The flowers come into first bloom about March 3, in the Wasco area, which is between average and late in comparison with other peaches in the neighborhood. The blossoms are small and non-showy. They are salmon-colored.

FRUIT

The mature fruit is slightly variable in size, ranging from medium to large. The axial diameter is from 2¾" to 3"; the diameter transverse the suture plane from 3¼" to 3⅝"; and the diameter at right angles to the suture plane, from 3¼" to 3¾". The form, like the size, is slightly variable and varies from globose to slightly unsymmetrical.

The suture is distinct but shallow, and extends from the base to the apex, where it becomes discontinuous. There is a slight depression beyond the pistil point.

The ventral surfaces are rounded and the lips unequal.

*Stem and stem cavity.*—The stem cavity is flaring in shape and elongated in the suture plane, with the suture showing on one side. The stem cavity is about half an inch deep, and about one inch broad. The base is rounded to truncate. The apex is short and varies from rounded to truncate; to slightly depressed. The pistil point is short and oblique.

The stem is from about 5/16" to approximately ½" in length. It is of medium caliper and nearly glabrous. It manifests a normal adherence to the stone.

*Skin.*—The skin is of medium thickness. It is tough, and tenacious to the flesh. It manifests no tendency to crack in a dry season. Its ground color is near to, but lighter than, Brilliant Greenish Yellow 7.5Y7/8 overlaid lightly to moderately with a color between Moderate Red 2.5R4/10 and Dark Red 2.5R3/7. The down varies from moderate to scant. It is short and rolls up when rubbed.

EATING QUALITY OF FRUIT

This description refers to a peach which was eating ripe at the time reported, in this case, on the 20th of August, 1979. The fruit had been picked in a firm/ripe state and stored indoors at room temperature for 3 days.

FLESH

The flesh was creamy white in color. The surface of the pit cavity was between Dark Reddish Orange, 7.5R4/11, and Dark Red, 5R3/7.

The amygdalin taste was scant; the juice abundant to moderate, and rich in viscosity. The texture was medium-fine and melting. The fibres were few and medium-tender.

The fruit had ripened evenly. Its flavor was mild and sweet. The aroma was pronounced. The eating quality was from good to best.

STONE

The stone is free. It has short fibres. The stone parts from the flesh smoothly but retains short fibre-like threads along the ridges. The size of the stone is medium, being about 1⅜" to 1¾" in length and ⅞" to 1-3/16" in breadth. Its thickness runs from 11/16" to ⅞". The form of the stone is oval but cuneate toward the apex. The base is slightly oblique; the hilum oblong. The apex is acute. The sides are unequal; the surface is irregularly furrowed throughout; it is ridged near the base and toward the apex and is pitted throughout. The ridges are jagged, toward the base and apex.

Some pits in the stone are circular and some are elongated. The ventral edge is medium-thick, and is without wing throughout.

The dorsal edge is medium-thick also with a relatively shallow broad groove; toward the base. Interrupted ridges are on either side.

The color of the stone is between Strong Brown 2.5YR4/7 and Moderate Reddish Brown, 10R3/4.

The stone shows no tendency to split.

The fruit has good marketing qualities, both as to keeping and shipping. It is used primarily as a dessert peach.

The variety has good resistance to insects and from good to medium resistance to diseases.

I claim:

1. A new and distinct variety of peach of the freestone class, substantially as herein shown and described, and further having, in combination, the following characteristics, namely: a moderately vigorous habit of growth, being a regular and heavy bearer, bearing small non-showy salmon-pink flowers and bearing fruit in mid-August which is somewhat larger than average, white-fleshed and globose, of eating quality from good to best, and having a moderate to abundant supply of rich, sweet juice.

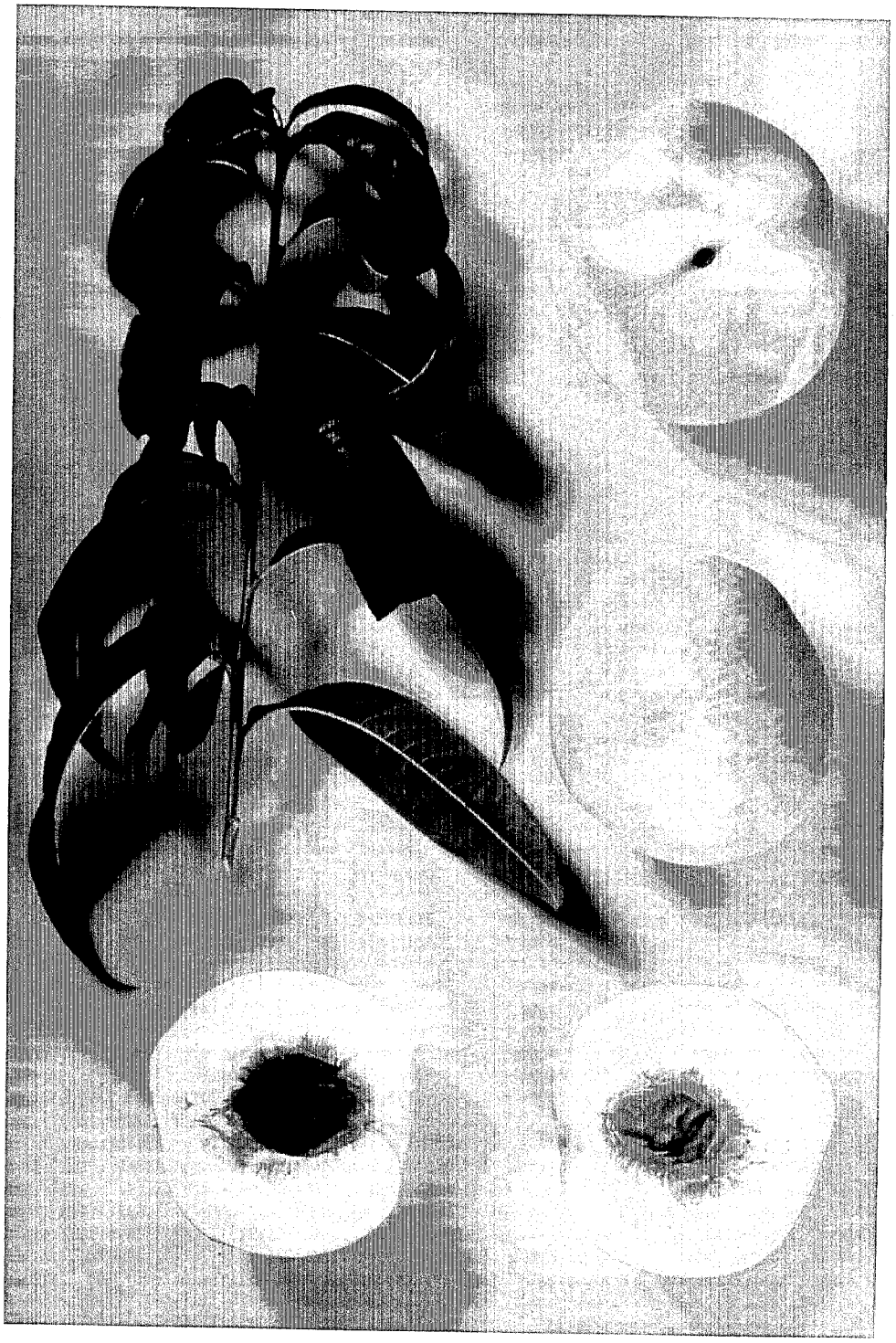

* * * * *